(12) United States Patent
Azar et al.

(10) Patent No.: US 9,681,925 B2
(45) Date of Patent: Jun. 20, 2017

(54) METHOD FOR AUGMENTED REALITY INSTRUMENT PLACEMENT USING AN IMAGE BASED NAVIGATION SYSTEM

(75) Inventors: Fred S. Azar, Princeton, NJ (US); Ali Khamene, Princeton, NJ (US); Frank Sauer, Princeton, NJ (US); Sebastian Vogt, Princeton, NJ (US)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 2439 days.

(21) Appl. No.: 11/107,640

(22) Filed: Apr. 15, 2005

(65) Prior Publication Data

US 2005/0251030 A1 Nov. 10, 2005

Related U.S. Application Data

(60) Provisional application No. 60/564,146, filed on Apr. 21, 2004.

(51) Int. Cl.
*A61B 5/05* (2006.01)
*A61B 90/00* (2016.01)
*A61B 34/20* (2016.01)
*A61B 90/11* (2016.01)
*A61B 34/10* (2016.01)

(52) U.S. Cl.
CPC .............. *A61B 90/36* (2016.02); *A61B 34/20* (2016.02); *A61B 90/11* (2016.02); *A61B 34/10* (2016.02); *A61B 90/361* (2016.02); *A61B 2034/107* (2016.02); *A61B 2090/365* (2016.02)

(58) Field of Classification Search
CPC ....... A61B 90/36; A61B 90/11; A61B 90/361; A61B 34/20; A61B 34/10
USPC ................ 600/424, 433, 434; 345/632, 633; 715/862
See application file for complete search history.

(56) References Cited

U.S. PATENT DOCUMENTS

| 5,512,827 | A | * | 4/1996 | Hardy et al. ................... 600/410 |
| 6,366,796 | B1 | * | 4/2002 | Yanof et al. ................... 600/407 |
| 6,535,756 | B1 | * | 3/2003 | Simon et al. ................. 600/424 |
| 2002/0140709 | A1 | * | 10/2002 | Sauer et al. .................. 345/633 |
| 2003/0120282 | A1 | * | 6/2003 | Scouten et al. ............... 606/130 |
| 2004/0106916 | A1 | * | 6/2004 | Quaid et al. ...................... 606/1 |

FOREIGN PATENT DOCUMENTS

WO WO 02100285 A1 12/2002

* cited by examiner

*Primary Examiner* — Joseph M Santos Rodriguez

(57) ABSTRACT

A system and method for instrument placement using an image based navigation system is disclosed. A target of interest is identified in a medical image of a patient. An image plane is displayed that goes through a center of the target. The image plane has a configurable orientation. The image plane is used to select a path for an instrument from a position on the patient's skin to the center of the target. A trajectory plane is viewed from a tip of the instrument to the center of the target. The trajectory plane reflects an orientation of the instrument. A particular trajectory plane is selected that is representative of a desired orientation of the instrument. An image of the particular trajectory plane is frozen. The instrument can then be inserted using a virtual guide and is navigated toward the target.

20 Claims, 4 Drawing Sheets

METHOD FOR AUGMENTED REALITY INSTRUMENT PLACEMENT USING AN IMAGE BASED NAVIGATION SYSTEM

CROSS-REFERENCE TO RELATED APPLICATION

This application claims the benefit of U.S. Provisional Patent Application Ser. No. 60/564,146, filed on Apr. 21, 2004, which is incorporated by reference in its entirety.

FIELD OF THE INVENTION

The present invention is directed to a method for augmented reality instrument placement using an image based navigation system, and more particularly, to a method for determining placement of a needle relative to a target so that a physician can determine the optimal path to the target.

BACKGROUND OF THE INVENTION

Augmented reality, also commonly referred to as augmented vision or augmented reality vision, augments an observer's view of the real world by superimposing computer generated graphical information. This information may be as simple as a text label attached to some object in the scene, or as complex as a 3D model of a patient's brain derived from an MRI scan and aligned to the real view of the person's head.

The observer may observe a real scene directly with his or her eyes, with the additional graphical information being blended therewith via a semi-transparent display located between the observer and the real scene. Such a display device can be, for example, a see-through head mounted display.

The display can also be opaque, like a computer screen or a non-see-through head mounted display. Such a display then presents to the observer the complete augmented view, i.e., a combination of the real-world view and the graphics overlay. A video camera takes the place of the real-world observer to capture the real world-view. For stereo vision, two cameras are required. A computer is used to combine the live video with the graphics augmentation.

The graphics have to be positioned, oriented, and scaled, or even rendered in a perspective fashion for correct alignment with the real-world view. It is desirable to "anchor" the graphics to a real-world object. To do this, the position and orientation of the camera with respect to the object, as well as the orientation of the object, must be known. That is, the relationship between two coordinate systems, one corresponding to the camera and the other corresponding to the object, must be known.

Tracking denotes the process of keeping track of the preceding relationship. Commercial tracking systems are available that are based on optical, mechanical, magnetic, inertial, and ultrasound measurement principles.

Augmented reality visualization can guide a user in manual mechanical tasks. For machine repair and maintenance scenarios, it has been suggested to augment the view with graphical pointers that show, e.g., which button to press or which screw to turn. Augmented reality visualization is also being suggested for medical applications where, e.g., biopsy needles have to be inserted into a target tumor without harming nearby nerves or where screws have to be inserted into bones at a precise location and in a precise direction.

As noted above, augmented reality visualization places virtual objects (computer generated graphics) into real scenes. The tracking of the vantage point, from which the real scene is viewed, with respect to a world coordinate system anchored at real world objects, allows the virtual objects to appear at desired locations in this world coordinate system. However, a correct visual interaction between real and virtual objects generally requires 3D information about the real objects. Disadvantageously, this 3D information is usually not available and, thus, the virtual objects are simply superimposed onto the image of the real scene. Accordingly, real objects can be hidden by virtual objects, although virtual objects cannot be hidden by real objects.

In addition, in medical applications there is an issue when a needle needs to be inserted in a procedure, such as a biopsy, that the needle takes a direct route to the target object without intersecting delicate structures, such as arteries or organs not of interest. In order for the physician to accurately guide the needle, it would be advantageous for the physician to know what potential obstacles are in its path. Accordingly, it would be desirable and highly advantageous to have a method for augmented reality instrument navigation so that the physician can determine an optimal path prior to insertion of a needle or other medical instrument.

SUMMARY OF THE INVENTION

The present invention is directed to a system and method for instrument placement using an image based navigation system. A target of interest is identified in a medical image of a patient. An image plane is displayed that goes through a center of the target. The image plane has a configurable orientation. The image plane is used to select a path for an instrument from a position on the patient's skin to the center of the target. A trajectory plane is viewed from a tip of the instrument to the center of the target. The trajectory plane reflects an orientation of the instrument. A particular trajectory plane is selected that is representative of a desired orientation of the instrument. An image of the particular trajectory plane is frozen. The instrument can then be inserted using a virtual guide and is navigated toward the target.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is directed to a system and method for augmented reality instrument placement using an image based navigation system. It is to be understood that the present invention may be implemented in various forms of hardware, software, firmware, special purpose processors, or a combination thereof. Preferably, the present invention is implemented as a combination of hardware and software. Moreover, the software is preferably implemented as an application program tangibly embodied on a program storage device. The application program may be uploaded to, and executed by, a machine comprising any suitable architecture.

Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures are preferably implemented in software, the actual connections between the system components (or the process steps) may differ depending upon the manner in which the present invention is programmed. Given the teachings herein, one of ordinary skill in the related art will be able to contemplate these and similar implementations or configurations of the present invention.

Figure 1:
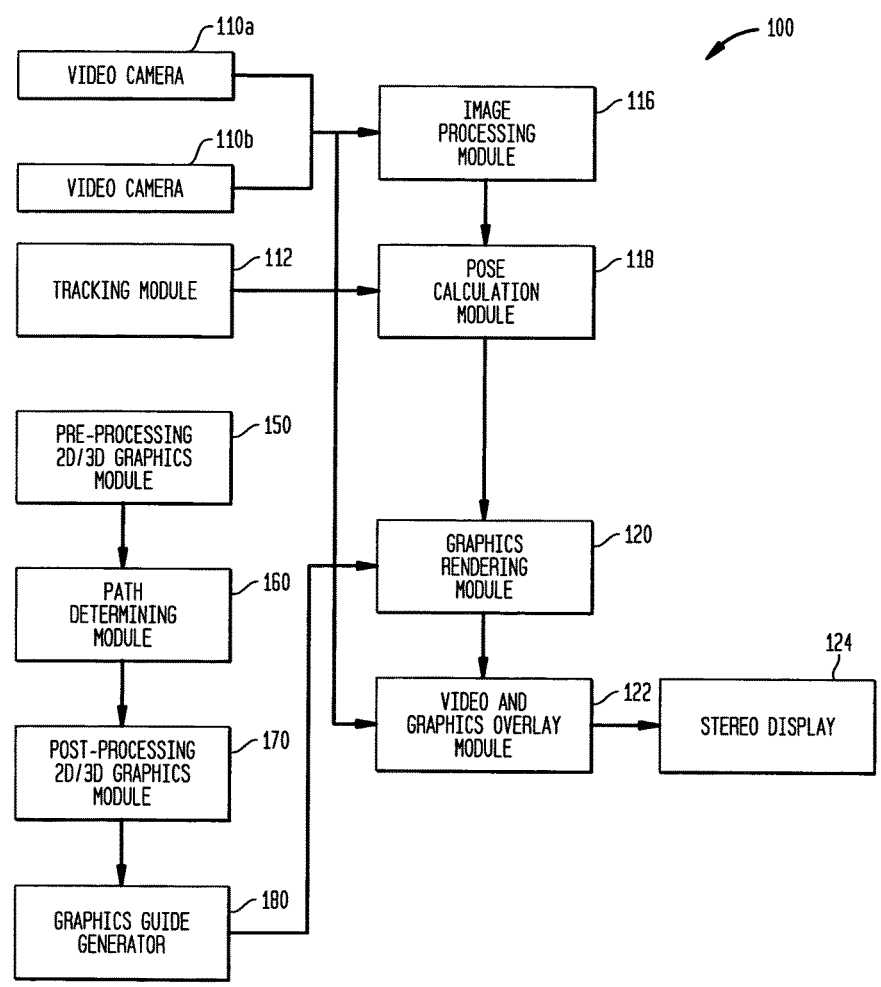
FIG. 1 is a block diagram of an augmented reality instrument navigation system, according to an illustrative embodiment of the present invention.

FIG. 1 illustrates a block diagram of an augmented reality instrument navigation system 100 according to an illustrative embodiment of the present invention. The system 100 includes: two video cameras 110a-b; a tracking module 112; a pre-processing 2D/3D graphics module 150; a path determining device 160; a post-processing 2D/3D graphics module 170; a graphics guide generator 180; an image processing module 116; a pose calculation module 118; a graphics rendering module 120; a video and graphics overlay module 122; and a stereo display 124. The two video cameras 110a-b and the stereo display 124 are employed to obtain 3D perception. Of course, other arrangements may be used (e.g., single video camera and non-stereo display) which maintain the spirit and scope of the present invention. In the illustrative embodiment of FIG. 1, the path determining module 160 and the graphics guide generator 180 are stand alone elements of the system 100. However, as readily appreciated by one of ordinary skill in the related, these elements may be integrated into other elements of the system 100 (e.g., the graphics rendering module 120). Given the teachings of the present invention provided herein, one of ordinary skill in the related art will contemplate these and various other configurations of the elements of FIG. 1, while maintaining the spirit and scope of the present invention.

The following description of the elements of FIG. 1 will be given with respect to augmented reality instrument navigation applications. The two video cameras 110a-b provide image related data corresponding to the real world to the system 100. The tracking module 112 provides data corresponding to the relationship between a user coordinate system (i.e., with respect to the vantage point of the user or the vantage point of the cameras that replace the eyes of the user), a coordinate system of the object (e.g., patient) to which the instrument is being applied and, optionally, an instrument coordinate system. The data provided by the tracking module 112 allows for the relationship(s) between the preceding coordinate systems to be known or finally calculated in the pose calculation module 118. The data provided through the pre-processing 2D/3D graphics module 150 may be, e.g., a Computer Tomographic (CT) scan or Magnetic Resonance (MR) image, preprocessed for a specific instrument positioning application. The data provided through the pre-processing 2D/3D graphics module 150 may also include geometrical information about the instrument. From information output from the pre-processing 2D/3D graphics module 150 to the path determining module 160, one or more potential paths for the instrument to travel and/or one or more potential target locations for the instrument to contact/penetrate may be determined as will be described in greater detail hereinafter. The path/target data as well as some data passed through the path determining module 160 from the pre-processing 2D/3D graphics module 150 is input to the post-processing module 170 which provides the data to the graphics guide generator 180 for use in generating graphics guides. It is to be appreciated that data which specifies one or more preferred types of graphics guides to be used during the positioning of the instrument may be input to the pre-processing 2D/3D graphics module 150 for ultimate use by the graphics guide generator 180 in selecting a type(s) of graphics guide to generate. Any type of known graphics guide may be selected to assist the physician in guiding the instrument along the selected path.

The image processing module 116 processes the image data provided from the two video cameras 110a-b. Processed image data from the image processing module 116 is input to the pose calculation module 118 along with the data provided from the tracking module 112. Data from the graphics guide generator 180 corresponding to one or more graphics guides is input to the graphics rendering module 120 along with the data output from the pose calculation module 118 so that the graphics can be rendered according to the camera pose, to be registered with respect to the object (to which the instrument is to be applied) seen in the video images. Rendered data is provided to the video and graphics overlay module 122 for subsequent display on the stereo display 124.

The present invention is directed to augmented reality instrument navigation with navigation graphics. The invention may be employed in the case when an instrument has to be positioned with a fairly high accuracy, and where a target or a target and a path can be selected and can be shown to the user using graphical guides or a trajectory plane in an augmented reality view. The navigation graphics mark the target. The navigation graphics also marks the final instrument position and/or orientation. Further, the navigation graphics marks the path to the final instrument pose. The user then aligns the instrument with a graphics guide or trajectory plane to perform his or her task. It is to be appreciated that the navigation of an instrument to a target without intersecting with critical organs or arteries is a problem that presents a significant obstacle to using augmented reality for instrument navigation.

Figure 2A:
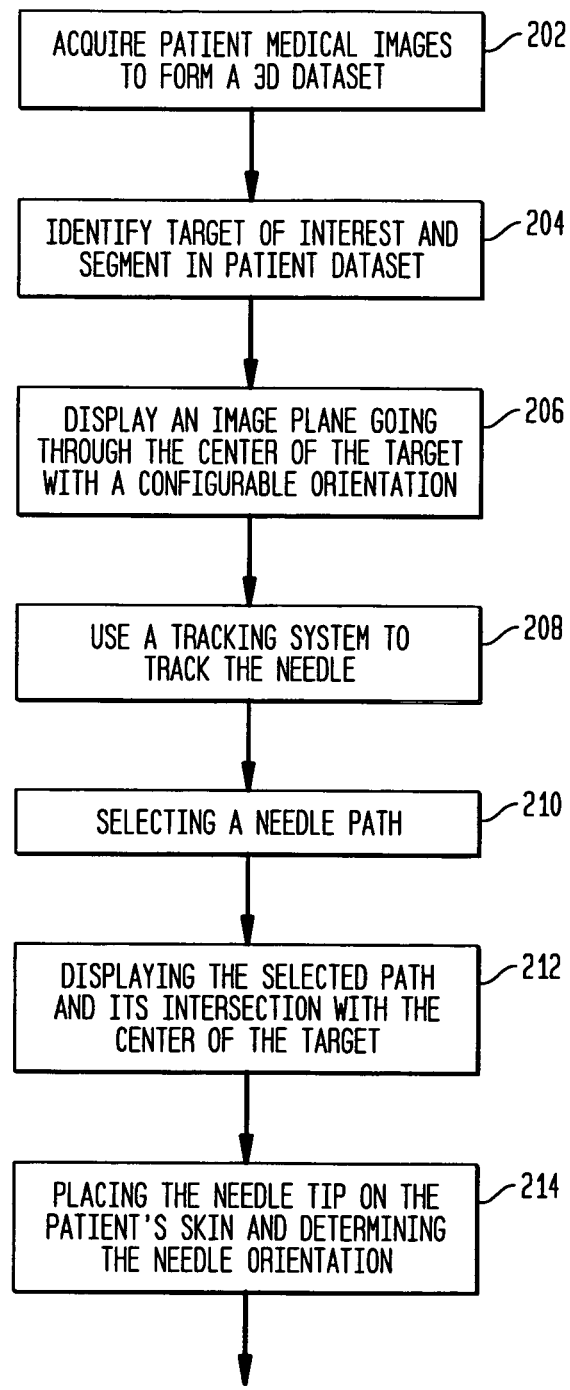
FIGS. 2A and 2B are a flow chart that illustrates a method for augmented reality instrument navigation in accordance with the present invention.
Figure 2B:
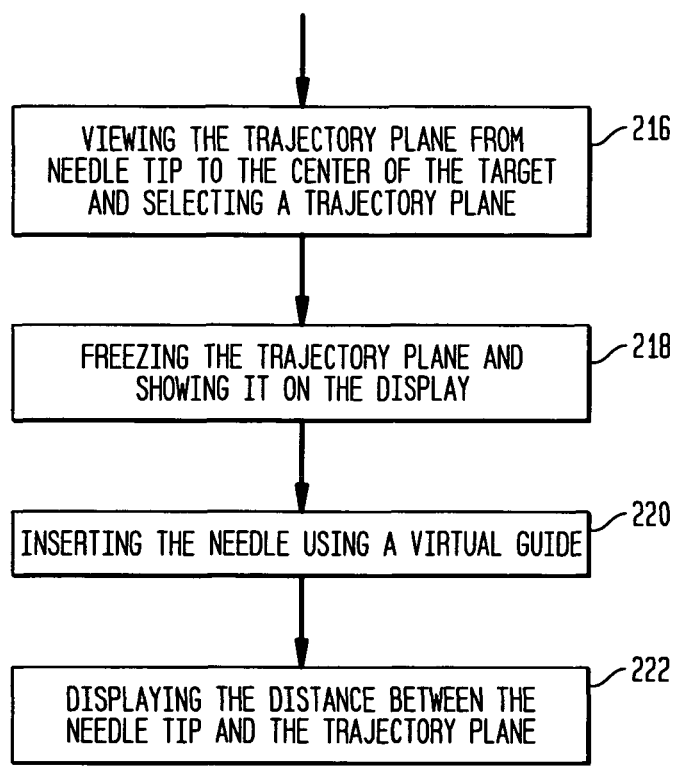

In accordance with the present invention, a method for augmented reality instrument navigation will now be described with reference to FIGS. 2A and 2B. It is to be understood by those skilled in the art that the workflow described hereinafter is applicable to a variety of navigation systems using different visualization schemes. These navigation systems can be two dimensional (2D) or three dimensional (3D) imaging modalities, stereoscopy on a monitor, or a head mounted display. Medical images for a patient are acquired to form a 3D dataset (step 202). As indicated above the images can be obtained using a variety of modalities such as Computed Tomography (CT), Magnetic Resonance Imaging (MRI) or ultrasound. A target of interest is identified and segmented in the patient dataset (step 204).

Prior to performing a procedure, the physician is shown an image plane going through the center of the target (step 206). The image plane has a configurable orientation that allows the physician to better discern the insertion point of the needle. Typically, the image plane is orthogonal to the general direction of needle insertion. The needle is then tracked using an optical tracking system (step 208). It is to be understood by those skilled in the art that other types of tracking system can be used without departing from the scope and spirit of the present invention.

The physician is able to select a safe and efficient needle path by moving the needle over the patient's skin (step 210). At each point that the needle is in contact with the patient's skin, the physician is able to observe the needle's virtual extended path and its intersection with the target image plane on a display. The display may be 2D or 3D and may appear on a monitor or a head mounted device. A path is selected and shown on the display once the needle's extended path intersects with the center of the target (step 212).

Next, the physician places the tip of the needle on the patient's skin and chooses the orientation of the needle (step 214). By moving the tip of the needle, the physician can view the image plane connecting the needle tip to the target and intersecting the target image plane (step 216). The physician can observe the position of any delicate structures that need to be avoided during needle insertion. Once the trajectory is selected, the physician can freeze the trajectory plane (step 218). Now the physician can see the target plane with the target and the trajectory plane showing clearly the chosen needle path from the patient skin to the target center.

Figure 3:
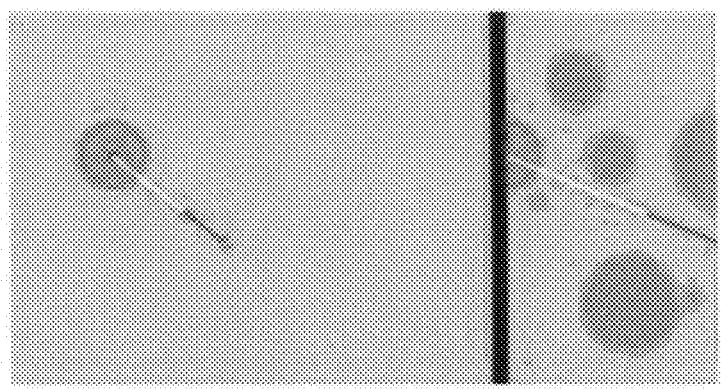
FIG. 3 illustrates an exemplary display depicting 2D image navigation during needle insertion in accordance with the present invention.
Figure 4:
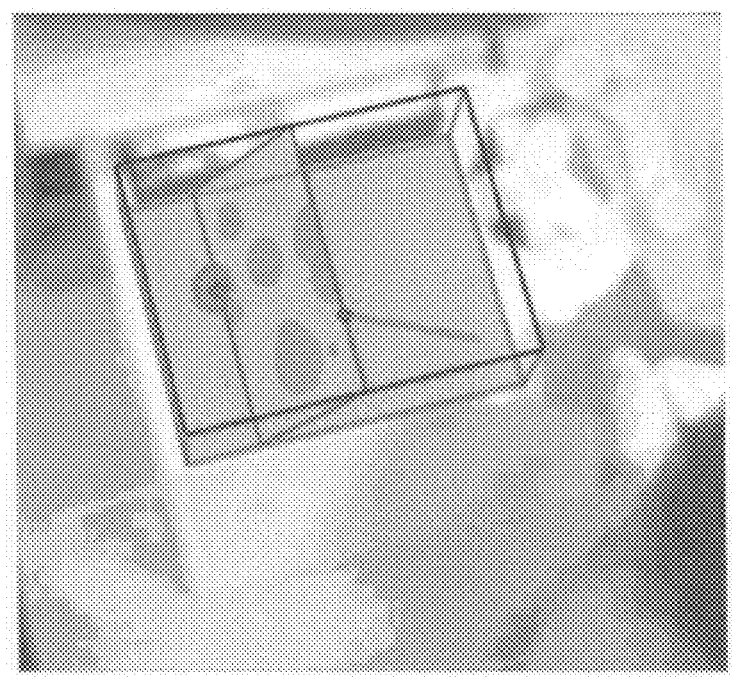
FIG. 4 illustrates an exemplary display depicting 3D based navigation during needle insertion in accordance with the present invention.

FIGS. 3 and 4 illustrate exemplary displays of 2D and 3D image navigation during needle insertion in accordance with the present invention. The 3D display is the same type of display that would be seen for HMD or stereoscopy images as well. As shown, a virtual path is display from the needle tip to the center of the target. The path direction and orientation are based on and essentially an extension of the orientation of the needle. In the 3D display, the image plane is also shown.

Next, the physician inserts the needle into the patient. A virtual guide can be used to help maintain the correct trajectory as the needle is inserted (step 220). While the needle is inserted, the display shows the distance between the needle's tip and the trajectory plane (step 222). As soon as the virtual guide shows the needle is aligned to the trajectory plane and the distance displayed matches zero, the physician has reached the target center. If the distance becomes negative, the needle has gone beyond the target center, and the physician can then easily correct the needle's position. Once the procedure is completed, the physician can remove the needle using the virtual guide in order to avoid delicate structures.

While the present invention has been described as a method for augmented reality instrument placement, the method of the present invention can also be utilized in a simple image-based or non-augmented reality system. A number of implementations could be incorporated to apply the instrument navigation. For example, a 3D augmented reality scene or 3D virtual reality scene could be displayed on a 2D screen. Alternatively, defined and relevant 2D planes could be displayed on a 2D screen. In such an instance the minimum hardware required would be a computer, a display, a tracking system and software similar to that described heretofore.

Having described embodiments for a method for augmented reality instrument placement using an image based navigation system, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A method for instrument placement using an image based navigation system comprising the steps of:
    displaying, in a three dimensional image, an image plane that goes through a center of a target of interest, the image plane having a configurable orientation;
    receiving user input configuring an orientation of an instrument; displaying, in the three dimensional image, a trajectory plane from the tip of the instrument to the center of the target, the trajectory plane reflecting a current orientation of the instrument and intersecting the image plane at the center of the target of interest, wherein the image plane is orthogonal to a direction of instrument insertions;
    displaying in the trajectory plane, the target of interest and potential obstacles in a path for the instrument from a position on a patient's skin to the center of the target;
    displaying in the trajectory plane a virtual extended path of the instrument from a point that a tip of the instrument is in contact with the patient's skin to the center of the target, the virtual extended path based on the current orientation of the instrument;
    receiving input selecting a particular trajectory plane representative of a desired orientation of the instrument; and
    freezing an image of the particular trajectory plane.

2. The method of claim 1 wherein the image based navigation system is an augmented reality system.

3. The method of claim 2 wherein the navigation system includes a head mounted display.

4. The method of claim 1 further comprising the steps of:
    displaying a virtual guide; and
    displaying a distance between the instrument tip and the image plane.

5. The method of claim 4 wherein when the distance reaches zero, the instrument has reached the center of the target.

6. The method of claim 4 wherein if the distance becomes negative, the instrument has gone beyond the center of the target.

7. The method of claim 1 wherein the step of receiving user input configuring the orientation of the instrument further comprises the step of tracking the instrument.

8. The method of claim 7 wherein an optical tracking system is used to track the instrument.

9. The method of claim 1 wherein the navigation system is a three dimensional imaging system.

10. The method of claim 1 wherein the instrument is a needle.

11. An imaging system for instrument navigation comprising:
    at least one camera for capturing images of an instrument and a patient;
    a display for displaying the images; and
    a processor for performing the following steps:

receiving the images;

displaying, in a three dimensional image, an image plane that goes through a center of a target of interest, the image plane having a configurable orientation;

receiving user input configuring an orientation of an instrument;

displaying, in the three dimensional image, a trajectory plane from the tip of the instrument to the center of the target, the trajectory plane reflecting a current orientation of the instrument and intersecting the image plane at the center of the target of interest, wherein the image plane is orthogonal to a direction of instrument insertion;

displaying in the trajectory plane, the target of interest and potential obstacles in a path for the instrument from a position on a patient's skin to the center of the target;

displaying in the trajectory plane a virtual extended path of the instrument from a point that a tip of the instrument is in contact with the patient's skin to the center of the target, the virtual extended path based on the current orientation of the instrument;

receiving input selecting a particular trajectory plane representative of a desired orientation of the instrument; and freezing an image of the particular trajectory plane.

12. The system of claim 11 wherein the imaging system is an augmented reality imaging system.

13. The system of claim 12 wherein the system further comprises a head mounted display.

14. The system of claim 11 wherein the processor further performs the steps of:

displaying a virtual guide to assist navigation of the instrument; and computing a distance between the instrument tip and the image plane.

15. The system of claim 14 wherein when the distance reaches zero, the instrument has reached the center of the target.

16. The system of claim 14 wherein if the distance becomes negative, the instrument has gone beyond the center of the target.

17. The system of claim 11 wherein the step of receiving user input configuring the orientation of the instrument further comprises the step of tracking the instrument.

18. The system of claim 11 wherein the system further comprises an optical tracking system for tracking the instrument.

19. The system of claim 11 wherein the imaging system is a three dimensional imaging system.

20. The system of claim 11 wherein the instrument is a needle.

* * * * *